US00PP27040P2

(12) United States Plant Patent
Smith et al.

(10) Patent No.: US PP27,040 P2
(45) Date of Patent: Aug. 9, 2016

(54) ***DENDRANTHEMA* PLANT NAMED 'RADIANT IGLOO'**

(50) Latin Name: *Dendranthema×morifolium*
Varietal Denomination: Radiant Igloo

(71) Applicants: Mark A. Smith, Fort Myers, FL (US); Cornelis P. Vandenberg, Fort Myers, FL (US)

(72) Inventors: Mark A. Smith, Fort Myers, FL (US); Cornelis P. Vandenberg, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 63 days.

(21) Appl. No.: 14/121,956

(22) Filed: Nov. 7, 2014

(51) Int. Cl.
*A01H 5/02* (2006.01)

(52) U.S. Cl.
USPC ..... Plt./289

(58) Field of Classification Search
USPC ..... Plt./289
See application file for complete search history.

*Primary Examiner* — Anne Grunberg
(74) *Attorney, Agent, or Firm* — C. A. Whealy

(57) ABSTRACT

A new and distinct cultivar of *Dendranthema* plant named 'Radiant Igloo', characterized by its upright, outwardly spreading and uniformly mounded to almost spherical plant habit; freely branching habit; dense and full plant form; uniform and freely flowering habit; decorative-type inflorescences; bright yellow-colored ray florets; natural season flowering occurs about September 14 to 24 in Pennsylvania; and good garden performance and winter hardiness.

2 Drawing Sheets

Botanical designation: *Dendranthema×morifolium.*
Cultivar denomination: 'RADIANT IGLOO'.

BACKGROUND OF THE INVENTION

The present invention relates to a new and distinct *Dendranthema* plant, botanically known as *Chrysanthemum×morifolium*, commercially grown as a perennial garden-type *Dendranthema* plant, and hereinafter referred to by the cultivar name 'Radiant Igloo'.

The new *Dendranthema* is the product of a planned breeding program conducted by the Inventors in Bogota, Colombia and Smoketown, Pa. The objective of the breeding program is to create new perennial garden-type *Dendranthema* plants having uniformly mounding plant habit, inflorescences with desirable inflorescence forms, attractive ray and disc floret shapes and colors, winter hardiness and good garden performance.

The new *Dendranthema* plant originated from a cross-pollination made by the Inventors in September, 2007, in Bogota, Colombia of *Chrysanthemum×morifolium* 'Frosty Yoigloo', disclosed in U.S. Plant Pat. No. 20,251, as the female, or seed, parent with a proprietary selection of *Chrysanthemum×morifolium* identified as code number H5537, not patented, as the male, or pollen, parent. The new *Dendranthema* plant was discovered and selected by the Inventors as a single flowering plant within the progeny of the stated cross-pollination in a controlled greenhouse environment in Smoketown, Pa. on Sep. 29, 2010.

Asexual reproduction of the new *Dendranthema* plant by vegetative cuttings was first conducted in a controlled greenhouse environment in Smoketown, Pa. in March, 2011 and such asexual propagation has shown that the unique features of this new *Dendranthema* plant are stable and reproduced true to type in successive generations.

SUMMARY OF THE INVENTION

Plants of the new *Dendranthema* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Radiant Igloo'. These characteristics in combination distinguish 'Radiant Igloo' as a new and distinct garden-type *Dendranthema* plant:

1. Upright, outwardly spreading and uniformly mounded to almost spherical plant habit.
2. Freely branching habit; dense and full plant form.
3. Uniform and freely flowering habit.
4. Decorative-type inflorescences.
5. Bright yellow-colored ray florets.
6. Natural season flowering occurs about September 14 to 24 in Pennsylvania.
7. Good garden performance and winter hardiness.

In side-by-side comparisons, plants of the new *Dendranthema* differ from plants of the female parent, 'Frosty Yoigloo' primarily in ray floret color as plants of 'Frosty Yoigloo' have white-colored ray florets. In addition, plants of the new *Dendranthema* are larger than plants of 'Frosty Yoigloo'.

In side-by-side comparisons, plants of the new *Dendranthema* differ from plants of the male parent selection primarily in inflorescence form as plants of the male parent selection have incurved-type inflorescences with numerous disc florets per inflorescence. In addition, plants of the new *Dendranthema* are larger than plants of the male parent selection.

Plants of the new *Dendranthema* can be compared to plants of *Chrysanthemum×morifolium* 'Sunny Yoigloo', disclosed in U.S. Plant Pat. No. 19,108. In side-by-side comparisons, plants of the new *Dendranthema* differ from plants of 'Sunny Yoigloo' in the following characteristics:

1. Plants of the new *Dendranthema* are slightly larger than plants of 'Sunny Yoigloo'.

2. Under low night temperatures conditions, plants of the new *Dendranthema* and 'Sunny Yoigloo' differ in ray flower color as plants of 'Sunny Yoigloo' will "pink" or "bronze" whereas plants of the new *Dendranthema* will retain their bright yellow ray floret coloration.

BRIEF DESCRIPTION OF THE PHOTOGRAPHS

The accompanying photographs illustrate the overall appearance of the new *Dendranthema* showing the colors as true as it is reasonably possible to obtain in colored reproductions of this type. Colors in the photographs may differ slightly from the color values cited in the detailed botanical description which accurately describe the colors of the new *Dendranthema* plant.

The photograph on the first sheet comprises a side perspective view of a typical flowering plant of 'Radiant Igloo' grown in a container.

The photograph on the second sheet is a close-up view of a typical flowering plant of 'Radiant Igloo'.

DETAILED BOTANICAL DESCRIPTION

The aforementioned photographs and following observations and measurements describe plants grown during the early autumn in 25-cm containers in a polyethylene-covered greenhouse in Lancaster, Pa. and under cultural practices typical of commercial garden-type *Dendranthema* production. During the production of the plants, day temperatures averaged 26.7° C. and night temperatures ranged from 15.6° C. to 18.3° C. Plants were five months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Radiant Igloo'.

Parentage:

*Female, or seed, parent.*—*Chrysanthemum×morifolium* 'Frosty Yoigloo', disclosed in U.S. Plant Pat. No. 20,251.

*Male, or pollen, parent.*—Proprietary selection of *Chrysanthemum×morifolium* identified as code number H5537, not patented.

Propagation:

*Type.*—Terminal vegetative cuttings.

*Time to produce a rooted young plant.*—About two weeks.

*Root description.*—Fine, fibrous; white in color.

*Rooting habit.*—Freely branching, dense.

Plant description:

*Plant and growth habit.*—Perennial garden-type *Dendranthema* plant with decorative-type inflorescences; upright, outwardly spreading and uniformly mounding to almost spherical plant habit; strong and vigorous growth habit.

*Branching habit.*—Freely branching habit, about primary lateral branches developing at potentially every node, each primary lateral with multiple secondary and tertiary branches; dense and full plant form; pinching is not required.

*Plant height.*—About 27.5 cm.

*Plant width.*—About 42 cm.

*Lateral branches.*—Length: About 21 cm. Diameter: About 3.75 mm. Internode length: About 1.25 cm. Strength: Strong. Texture: Pubescent, minute; longitudinally ridged. Color: Close to 146A.

*Leaves.*—Arrangement: Alternate, simple. Length: About 3.1 cm. Width: About 2.2 cm. Apex: Cuspidate. Base: Attenuate. Margin: Palmately lobed, sinuses between lateral lobes mostly parallel to divergent. Texture, upper surface: Smooth, glabrous. Texture, lower surface: Pubescent, minute; veins prominent on lower surface. Venation pattern: Pinnate. Color: Developing and fully expanded leaves, upper surface: Close to N137A; venation, close to 137A. Developing and fully expanded leaves, lower surface: Close to 137B; venation, close to 146A to 146B. Petioles: Length: About 9 mm. Diameter: About 3 mm. Texture, upper surface: Smooth, glabrous. Texture, lower surface: Pubescent; minute. Color, upper surface: Close to N137A. Color, lower surface: Close to 137B.

Inflorescence description:

*Type and arrangement.*—Decorative-type inflorescence form with elongated oblong-shaped ray florets; disc and ray florets arranged acropetally on a capitulum; inflorescences face mostly upright to outwardly and held above and beyond the foliar plane on strong peduncles.

*Fragrance.*—None detected.

*Flowering response.*—Under natural season conditions, plants flower about September 14 to 24 in Pennsylvania.

*Postproduction longevity.*—Inflorescences maintain good color and substance for about three to six weeks on the plant depending on temperatures; inflorescences persistent.

*Quantity of inflorescences.*—Freely flowering habit with about five inflorescences developing per lateral branch.

*Inflorescence buds.*—Height: About 4 mm. Diameter: About 4 mm. Shape: Oblate to spherical. Color: Close to N137B.

*Inflorescence size.*—Diameter: About 2.5 cm. Depth (height): About 1.25 cm. Disc diameter: About 2 mm. Receptacle diameter: About 3.5 mm. Receptacle height: About 4.5 mm.

*Receptacle color.*—Close to 144B.

*Ray florets.*—Quantity and arrangement: About 112 ray florets develop per inflorescence and arranged in numerous whorls. Length: About 1.6 cm. Width: About 3 mm. Shape: Elongated oblong. Apex: Retuse to emarginate. Base: Attenuate and then fused into a short tube. Margin: Entire. Orientation: Initially upright, then arching outwardly. Texture, upper and lower surfaces: Smooth, glabrous; velvety; longitudinally ribbed. Color: When opening, upper surface: Close to 6A; at the base, close to 144A. When opening, lower surface: Close to 6A to 6B. Fully opened, upper surface: Close to 6A; at the base, close to 144A; color does not fade with development. Fully opened, lower surface: Close to 6A to 6C; color does not fade with development.

*Disc florets.*—Quantity and arrangement: About 22 fused disc florets develop per inflorescence and massed at the center of the capitulum; inconspicuous. Length: About 4 mm. Diameter: About 1.5 mm. Shape: Tubular, elongated. Apex: Five-pointed. Texture, inner and outer surfaces: Smooth, glabrous.

Color, mature: Apex: Close to 12A. Mid-section: Close to 144A. Base: Close to NN155D.

*Phyllaries*.—Quantity and arrangement: About 18 phyllaries develop per inflorescence and arranged in about two to three whorls. Length: About 6 mm. Width: About 2 mm. Shape: Lanceolate. Apex: Acute. Base: Truncate, fused. Margin: Entire; membraneous. Texture, upper surface: Smooth, glabrous. Texture, lower surface: Pubescent, minute. Color, upper and lower surfaces: Close to 137A.

*Peduncles*.—Length, terminal peduncle: About 3.4 cm. Length, fourth peduncle: About 4.75 cm. Diameter, terminal peduncle: About 1.5 mm. Angle: Mostly upright or curving upright. Strength: Strong, wiry. Texture: Pubescent; minute. Color: Close to 146A.

*Reproductive organs*.—Androecium (present on disc florets only): Stamen number: Five per floret. Filament length: About 4.5 mm. Filament color: Close to 150D. Anther length: Less than 1 mm. Anther shape: Narrowly oblong. Anther color: Close to 12A. Pollen amount: None observed. Gynoecium (present on ray and disc florets): Pistil length: About 5 mm. Stigma shape: Bi-parted. Stigma color: Close to 6A. Style length: About 4.5 mm. Style color: Close to 150D. Ovary color: Close to 144A.

*Seeds and fruits*.—Seed and fruit production has not been observed on plants of the new *Dendranthema*.

Disease & pest resistance: Resistance to pathogens and pests common to *Dendranthema* plants has not bee observed on plants of the new *Dendranthema* grown under commercial production conditions.

Garden performance & temperature tolerance: Plants of the new *Dendranthema* have demonstrated excellent garden performance, are hardy to USDA Zone 5 and tolerate high temperatures about 37.8° C.

It is claimed:

1. A new and distinct *Dendranthema* plant named 'Radiant Igloo' as illustrated and described.

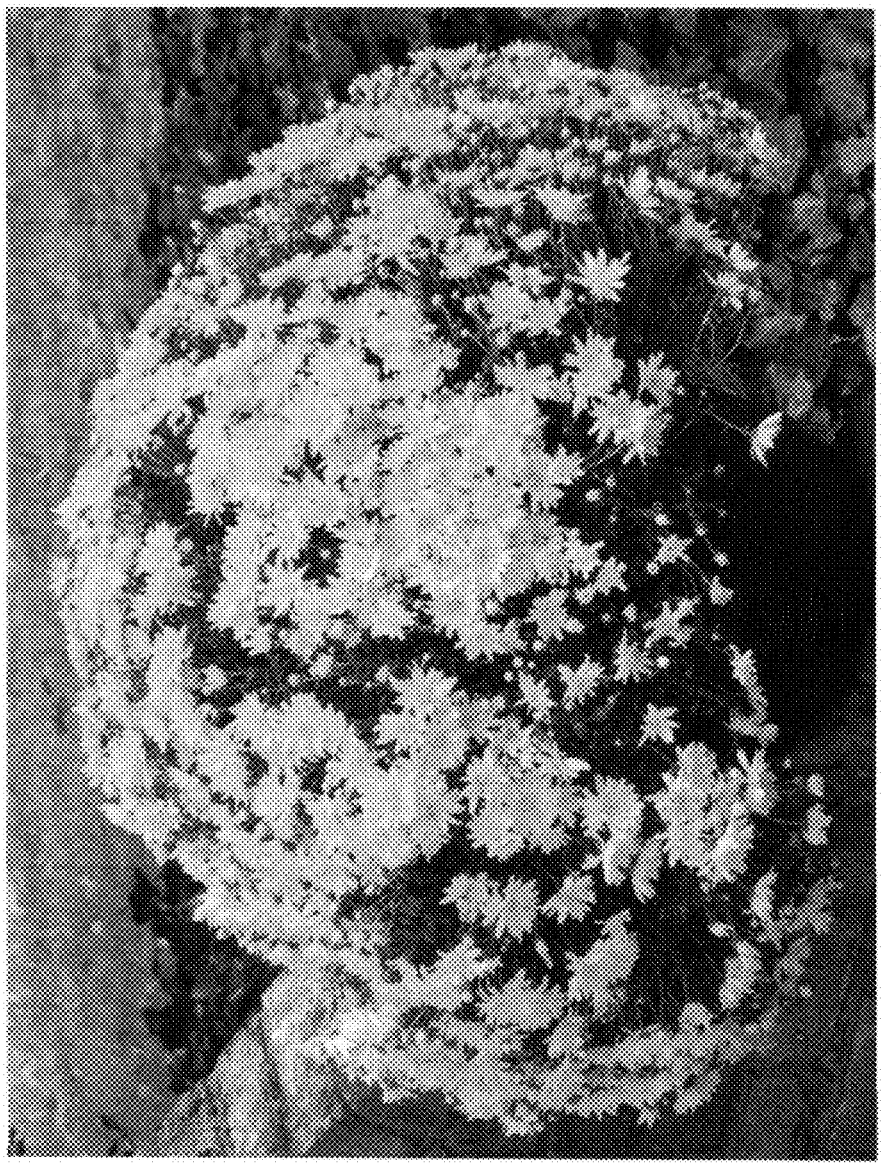

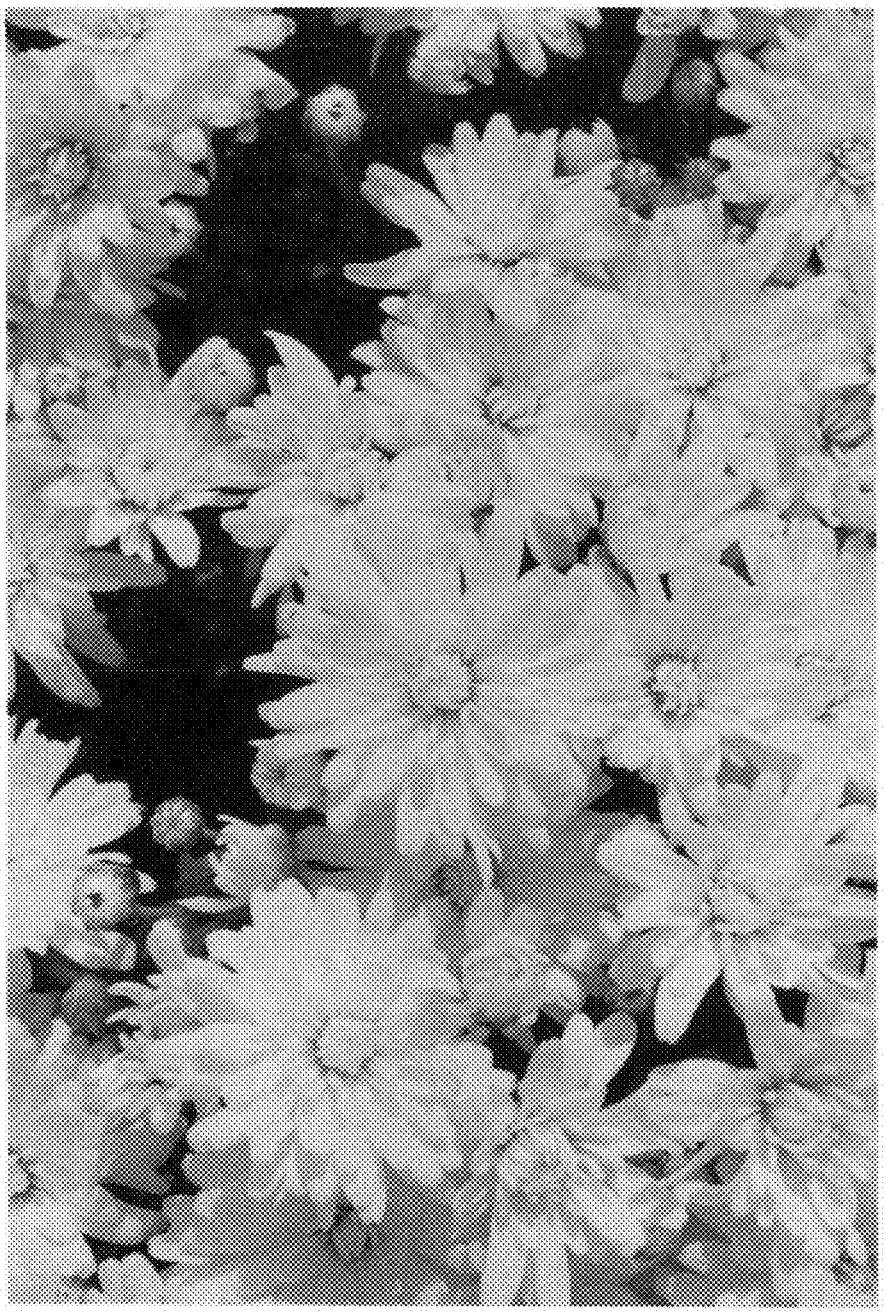

* * * * *